United States Patent [19]

Thorogood

[11] 4,284,641

[45] Aug. 18, 1981

[54] PHARMACEUTICALLY ACTIVE IMIDAZOLE DERIVATIVES

[75] Inventor: Peter B. Thorogood, London, England

[73] Assignee: Burroughs Wellcome Co., Research Triangle Park, N.C.

[21] Appl. No.: 936,406

[22] Filed: Aug. 24, 1978

[30] Foreign Application Priority Data

| Aug. 26, 1977 | [GB] | United Kingdom | 35912/77 |
| Aug. 26, 1977 | [GB] | United Kingdom | 35913/77 |
| Feb. 1, 1978 | [GB] | United Kingdom | 3983/78 |
| Feb. 1, 1978 | [GB] | United Kingdom | 3984/78 |
| Aug. 8, 1978 | [GB] | United Kingdom | 32526/78 |
| Aug. 8, 1978 | [GB] | United Kingdom | 32536/78 |
| Aug. 22, 1978 | [GB] | United Kingdom | 34106/78 |

[51] Int. Cl.$^3$ .......................................... A61K 31/415
[52] U.S. Cl. ................................ 424/273 R; 548/335
[58] Field of Search ..................... 548/335; 424/273 R

[56] References Cited

U.S. PATENT DOCUMENTS

| 3,541,109 | 11/1970 | Kaner . | |
| 3,637,731 | 1/1972 | Johnson . | |
| 3,843,676 | 10/1974 | Spaening et al. | 548/335 |
| 3,927,017 | 12/1975 | Heeres et al. . | |
| 3,991,201 | 11/1976 | Heeres et al. . | |
| 4,006,243 | 2/1977 | Strehike et al. . | |
| 4,036,975 | 7/1977 | Walker et al. | 424/273 |
| 4,115,578 | 9/1978 | Miller . | |

FOREIGN PATENT DOCUMENTS

| 719664 | 8/1968 | Belgium . | |
| 1213413 | 3/1966 | Fed. Rep. of Germany . | |
| 2533211 | 2/1977 | Fed. Rep. of Germany . | |
| 1603793 | 7/1971 | France . | |
| 46-24143 | 7/1971 | Japan | 348/335 |
| 6706104 | 5/1967 | Netherlands | 548/335 |
| 1122717 | 5/1967 | United Kingdom . | |
| 1364312 | 8/1974 | United Kingdom . | |

OTHER PUBLICATIONS

Ito et al., Tetrahedron Letters, 18, pp. 1535–1538, 1938.
Tai & Yuan, Biochem. Biophys. Res. Comm., 80 (1), 236–242 (1976).
S. Iwasaki, Helv. Chim. Acta, 59 (8), 2753–2764, (1976).
S. Iwasaki, Helv. Chim. Acta, 61 (8), 2831–2842 (1978).
Leusen et al., Chem. Abstracts, vol. 86, 1977, 189795c.
Fournari et al., Chem. Abstracts, vol. 69, 1968, 106622u.
Schubert et al., Chem. Abstracts, vol. 60, 1964, 14494h.
Jones et al., Canada Journal of Chemistry, vol. 49, 1971, pp. 325–332.
Prostaglandins 13, Moncada et al., pp. 611–618, 1977.
Biochem. Pharmacol. 24, pp. 1902–1903, 1975.
Biochem. Pharmacol., 23, pp. 2377–2386, 1974.
Maslinski et al., Agents and Actions, vol. 3/3, 1973.
Fournari et al., Bull. Soc. Chimique, 6, pp. 2438–2446, A68.
Leusen et al., Jour. Org. Chem. 42, 1153–1159, 1977.
Schubert et al., Wissenschaftliche Zeitschrift, X1/5, 603–611 (1962).
Jones et al., Canadian Jour. Chem., vol. 49, 325–332, (1971).

*Primary Examiner*—Henry R. Jiles
*Assistant Examiner*—Jane T. Fan
*Attorney, Agent, or Firm*—Donald Brown

[57] ABSTRACT

The invention relates to a class of imidazoles substituted by cycloalkyl or cycloalkenyl which have pharmacological properties making them useful in medicine, in particular in the prophylaxis and treatment of thromboembolic disorders.

76 Claims, No Drawings

PHARMACEUTICALLY ACTIVE IMIDAZOLE DERIVATIVES

The present invention relates to imidazole derivatives and salts thereof, to their synthesis and intermediates therefor, to pharmaceutical formulations containing such compounds and to the use of these compounds in medicine.

Thromboxane $A_2$ ($TXA_2$), a potent stimulator of blood platelet aggregation, is produced, in platelets, from the prostaglandin endoperoxides $PGG_2$ and $PGH_2$. Prostacyclin ($PGI_2$), which has potent anti-aggregatory activity, is also produced (in blood vessel walls) from $PGG_2$ and $PGH_2$ and it has been suggested that a balance between the production of $TXA_2$ and $PGI_2$ is the controlling factor in thrombus formation. It would, in consequence, be desirable in the treatment and prophylaxis of thrombo-embolic disorders to be able to selectively inhibit $TXA_2$ synthetase, thereby favouring the production of the anti-aggregatory agent $PGI_2$.

Imidazole and 1-methylimidazole are known to provide some degree of inhibition of the enzymic conversion of the endoperoxides ($PGG_2$ and $PGH_2$) to thromboxane $A_2$ by platelet microsomes (Moncada et al., Prostaglandins, 13/4, 611–618, 1977). Certain 1-n-alkylimidazoles, especially 1-n-dodecylimidazole and its higher homologues have been described as being capable of lowering serum cholesterol levels (U.K. Pat. No. 1 364 312; Biochem. Pharmacol. 24, 1902–1903, 1975).

We have now discovered that $TXA_2$ synthetase may be inhibited by 1-alkylimidazoles of formula (I) and acid addition salts thereof. The compounds of formula (I) and their salts are hereinafter referred to as the "active compounds".

The compounds of formula (I) are:

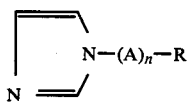
(I)

in which A is a straight or branched, saturated or unsaturated acyclic hydrocarbon radical of from 1 to 3 carbon atoms, n is 0 or 1, and R is a cycloalkyl or cycloalkenyl radical of from 4 to 9, preferably from 5 to 8, carbon atoms and optionally substituted by one, two, three or more alkyl radicals each containing from 1 to 4 carbon atoms, or, when n is 1, A and R together form an alkyl radical of from 4 to 7 carbon atoms or an alkenyl or alkynyl group of from 4 to 9 carbon atoms.

A novel class of compounds within the scope of formula (I) are those of formula (Ia):

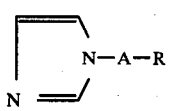
(Ia)

in which A is a straight or branched, saturated or unsaturated acyclic hydrocarbon radical of from 1 to 3 carbon atoms and R is a cycloalkyl or cycloalkenyl radical of from 4 to 9, preferably from 5 to 8, carbon atoms and optionally substituted by one, two, three or more alkyl radical each containing from 1 to 4 carbon atoms, with the proviso that when A is a methylene radical, R is not unsubstituted cyclohexyl.

In formula (I) and (Ia) examples, cycloalkyl radicals are cyclobutyl, cyclopentyl, cyclohexyl, cycloheptyl and cyclooctyl; cycloalkenyl radicals include cyclohex-3-enyl, cyclopentenyl, and 1,4-cyclohexadienyl; alkenyl radicals include pent-2-enyl and pent-4-enyl.

A valuable class of compounds of formula (I) are those in which n is 1, R is cyclohexyl, cycloheptyl, cyclooctyl, or cycloalkenyl of 6 to 8 carbon atoms, and A is —$CH_2$— or —$(CH_2)_2$—. Compounds of formula (I) or (Ia) may also be used as acid addition salts thereof, especially as pharmaceutically acceptable ones. Especially preferred compounds include:

1-Cyclooctylmethylimidazole
1-Cyclohex-3-enylmethylimidazole
1-Cyclohexylethylimidazole
and acid addition salts thereof.

Other potent compounds include:
1-Cyclopentylmethylimidazole
1-Cyclooctylvinylimidazole
1-(1-Cyclooctylethyl)imidazole
1-(2-Cyclooctylethyl)imidazole
1-(3-Cyclooctylpropyl)imidazole
1-(Cycloheptylmethyl)imidazole
1-(Cyclohept-2-enylmethyl)imidazole
1-Cyclononylmethylimidazole
1-(4-Methylcyclohexylmethyl)imidazole
1-(Cyclobutylmethyl)imidazole
1-Cycloheptylimidazole
1-Cyclopentylimidazole
1-Cyclohexylmethylimidazole
1-n-Butylimidazole
1-n-Pentylimidazole
1-n-Hexylimidazole
1-Pent-2-enylimidazole
1-Pent-4-enylimidazole
1-(3-Methylbutyl)imidazole
and acid addition salts thereof.

In contrast to imidazole and 1-methylimidazole the compounds of formula (I) are more potent inhibitors of $TXA_2$ synthetase. Many of the compounds (for example in (I) R is cycloalkyl or cycloalkenyl, n is 1, and A is —$CH_2$— or —$(CH_2)_2$— are also more selective in their action in not inhibiting other prostaglandin-generating enzymes such as cyclo-oxygenase. The compounds of formula (I) also do not produce the side-effects found with imidazole upon in vivo administration. The compounds of formula (I) are further capable of inhibiting platelet aggregation in vivo and also are capable of disaggregating platelet clumps. The compounds 1-cyclooctylmethylimidazole, 1-cyclohex-3-enylmethylimidazole and 1-cyclohexylethylimidazole and their salts especially displaying these properties.

Imidazoles of formula (I) and acid addition salts thereof may be made by any method known in the art for the synthesis of compounds of analogous structure. In general these methods comprise linking the imidazole ring to the remainder of the molecule; converting a precursor molecule by elimination of a functional group from the imidazole ring; and formation of the desired compound from a corresponding imidazoline, pyrazole or unsaturated analogue.

A most convenient method of synthesis involves the reaction of imidazole (formula II) or a salt thereof with an alkylating agent of formula (III):

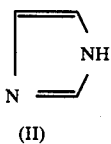 

(II)    (III)

(VI)

wherein R and A are as defined in formula (I) and Z is a leaving group. This reaction is well established in the literature, and the leaving group may be chosen from a variety of substituents but especially halo, preferably chloro or bromo, or from p-toluenesulphonyloxy but other arylsulphonyloxy, alkanesulphonyloxy or aralkylsulphonyloxy radicals may be used. The reaction is preferably performed in the presence of an acid acceptor, for example an alkali metal alkoxide such as sodium methoxide or potassium tertiary butoxide in the presence of the corresponding alkanol. The leaving group Z may itself be formed in situ from the corresponding alkanol (Z=OH) by reaction with a hydrohalogenic acid (e.g. hydrochloric acid or a Lewis acid such as aluminium chloride: see Japanese Patent Kokai No. 131577/77) and the resulting agent of formula (II) reacted directly with imidazole without prior isolation. Alternatively an alkanol (Z=OH) or a derivative thereof (e.g. Z=R—A—O—) may be reacted directly with imidazole (II) by heating in the presence of a dehydrating agent such as phosphoric acid, or a phosphate (see Japanese Patent Publication No. 5 1105 060), sulphuric acid or sulphates (see Japanese Patent Publication No. 5 1105 061).

Among precursor molecules which may be converted to a compound of formula (I) or an acid addition salt thereof, are substituted imidazole derivatives of formula (IV) or addition salts thereof

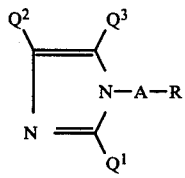

(IV)

wherein A and R are as defined in formula (I), and $Q^1$, $Q^2$ and $Q^3$ are the same or different, at least one being a radical capable of removal by for example reduction or oxidation, the other being a radical having the same function or is hydrogen. $Q^1$, $Q^2$ and $Q^3$ may be selected from thio (—SH), alkylthio (-Salkyl wherein alkyl has 1 to 4 carbon atoms) or halo preferably chloro or bromo. The reaction conditions are chosen according to the nature of the radicals $Q^1$, $Q^2$ and $Q^3$. Desulphurisation may be performed by oxidative or reductive procedures using for example nitric acid or Raney nickel; and reductive dehalogenation by the use of zinc and acetic acid or Raney nickel or other reagents known in the literature.

Another class of precursors include mono- or dicarboxyimidazoles or derivatives thereof of formula (VI):

wherein A and R are as defined in formula (I), at least one of $R^1$, $R^2$ and $R^4$ is carboxyl or a derivative thereof (for example an ester such as an alkyl ester, an acid halide such as the chloride, or the nitrile) and the other is hydrogen or carboxyl or a derivative as described. The compounds of formula (VI) may be converted into the imidazoles of formula (I) by any suitable decarboxylation conditions which may simply comprise heating the compounds with or without a catalyst such as copper.

The imidazoles of formula (I) may also be made from a compound of formula (VII):

(VII)

wherein $\underline{N}$ is 1-imidazoline, 1-imidazole or 1-pyrazole, $A^1$ is a straight or branched saturated or unsaturated acyclic hydrocarbon radical, and $R^3$ is a cycloalkyl or cycloalkenyl radical of from 4 to 9 carbon atoms optionally substituted by alkyl as defined in formula (I), provided that at least one of $\underline{N}$, $A^1$ and $R^3$ is other than limidazole, a saturated acyclic hydrocarbon and an optionally substituted cycloalkyl group respectively as defined in formula (I). Thus an imidazoline (VIII):

(VIII)

wherein A and R are defined in formula (I) may be dehydrogenated to the corresponding imidazole in the presence of a catalyst for example by heating to 250° C. in the presence of palladium, nickel or platinum under pressure, or by heating with a dehydrogenating agent such as selenium or copper oxide. The 1-pyrazole compounds (VII) may be treated with ultra-violet irradiation, optionally under an inert atmosphere (e.g. argon) in for example 1,2-dimethoxyethane at room or elevated temperatures (see for example "Ring Transformations of Heterocycles" edited van der Plas, Academic Press, 1973 at page 261). The unsaturated imidazoles of formula (I) (in formula (VIII), $A^1$ and/or $R^3$ are unsaturated) may be reduced to the corresponding saturated compounds with a noble metal catalyst, for example platinum or palladium in an alkanol.

The intermediates for use in the above described reactions may also be made by conventional methods known in the art. Thus the 1-pyrazole and 1-imidazoline intermediates (formula (VII)) may be prepared by alkylation of pyrazole and imidazoline in an analogous manner to that described above for preparation of the corresponding imidazoles. The intermediates of formula (III) may be made in known manner preferably by halogenation of the corresponding alcohols (formula (III), Z=—OH) where in such compounds R is cycloalkenyl; the alcohol is conveniently prepared by the Prins reaction from the cycloalkene and paraformaldehyde (Bull.

Chem. Soc. Japan 46/8, 2512-5, 1973). The substituted imidazole intermediates of formula (IV) may be made in known manner, for example see "Imidazole and its derivatives" Part I, Ed. K. Hofmann, Interscience Publishers Inc. New York, 1973. For example the 2-thioimidazoles of formula (IV) may be made by cyclisation of an acetal of formula (IX):

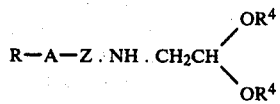

with thiocyanate, wherein $R^4$ is alkyl.

The pharmaceutically acceptable addition salts of the compounds of formula (I) may be prepared by any method known in the art. In particular they may be prepared by treating the parent imidazole with the appropriate acid.

Examples of the addition salts of the compounds of formula (I) include those salts derived from the following acids: oxalic, hydrochloric, hydrobromic, sulphuric, nitric, perchloric, fumaric, maleic, phosphoric, glycolic, lactic, salicyclic, succinic, toluene-p-sulphonic, tartaric, acetic, citric, methanesulphonic, formic, benzoic, malonic, naphthalene-2-sulphonic and benzenesulphonic.

The imidazoles of formula (I) may be used in conjunction with a phosphodiesterase inhibitor, which provides a further, synergistic increase in effect, as it acts against platelet aggregation by a different pathway.

Suitable phosphodiesterase inhibitors for use in potentiating the anti-aggregatory effects of the active compounds include as such or as pharmaceutically acceptable salts:

(a) Xanthine derivatives such as:
Theophylline(3,7-dihydro-1,3-dimethyl-1H-purine-2,6-dione), and salts thereof.
3-Isobutyl-1-methyl-xanthine;
Caffeine(3,7-dihydro-1,3,7-trimethyl-1H-purine-2,6-dione) and salts thereof; and
Aminophylline (adduct of Theophylline and 1,2ethanediamine (2:1)).

(b) Isoquinoline derivatives, for example:
Papaverine(1-[(3,4-dimethoxyphenyl)methyl]6,7-dimethoxyisoquinoline) and salts thereof; and
6,7-Diethoxy-1-(4,5-diethoxybenzyl)isoquinoline or its salts e.g. its hydrochloride;

(c) Derivatives of pyrimido(5,4-d)-pyrimidine, for example:
Dipyridamole(2,2',2'',2'''-(4,8-dipiperidinopyrimido[5,4-d]pyrimidin-2,6-diyldinitrilo)tetraethanol) and its salts;
2,2',2'',2'''-[[4-(1-piperidinyl)pyrimido[5,4-d]pyrimidin-2,6-dily]dinitrilo]tetrakisethanol and its salts; and
2,4,6-tri-4-morpholinylpyrimido[5,4-d]pyrimidine and its salts.

(d) Derivatives of thieno[3,2-d]pyrimidine, for example:
N-[4-(4-morpholinyl)thieno]3,2-d[pyrimidin-2-yl]1,2-ethanediamine.

(e) Derivatives of pyrazolo[3',4':2,3]pyrido[4,5-b][1,5]benzodiazepin-6-(3H)-one, for example:
3-Ethyl-7,12-dihydro-7,12-dimethyl-pyrazolo[4',3':5,6]pyrido[4,3-b]-[1,5]benzodiazepin-6-(3H)-one;
3-Ethyl-7,12-dihydro-9-methoxy-7,12-dimethyl-pyrazolo[3',4':2,3]pyrido[4,5-b]]1,5]benzodiazepin-6-(3H)-one; and
10-Chloro-3-ethyl-7,12-dimethyl-7,12-dihydropyrazolo[4',3':5,6]pyrido[4,3-b] [1,5]benzodiazepin-6-(3H)-one.

(f) Derivatives of 1H- or 2H-pyrazolo[3,4-b]-pyridne, for example:
4-(Butylamino)-1-ethyl-1H-pyrazolo[3,4-b]pyridine-5-carboxylic acid ethyl ester;
4-(Butylamino)-1H-pyrazolo[3,4-b]pyridine-6-carboxylic acid ethyl ester;
4-Chloro-1-ethyl-3-methyl-1H-pyrazolo[3,4-b]pyridine-5-acetonitrile;
1-Ethyl-4-(isopropylidenehydrazino)-3-methyl-1H-pyrazolo[3,4-b]pyridine-5-carboxylic acid ethyl ester or its salts such as its hydrochloride hemihydrate; and
2-Methyl-6-phenyl-4-(1-piperidinyl)-2H-pyrazolo[3,4-b]pyridine or its salts e.g. its hydrochloride.

(g) Derivatives of 5H-furo-[3,4-e]pyrazolo[3,4-b]pyridine-5-one, for example:
4-(Butylamino)-1-ethyl-1,7-dihydro-7-hydroxy-5H-furo-[3,4-e]pyrazolo[3,4-b]pyridine-5-one; and (h) Derivatives of 1(2H)-naphthalenone, for example:
2[(Dimethylamino)methyl]-3,4-dihydro-7-methoxy-1(2H)-naphthalenone or its salts e.g. its 1:1 hydrochloride.

The active compounds are particularly useful in the treatment and/or prophylaxis of thrombo-embolic disorders in mammals, including man. It is to be understood that the term "thrombo-embolic disorders" includes those disorders whose etiology is associated with platelet aggregation.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts cerebro-vascular thrombosis and ischaemic peripheral vascular disease; to treat and prevent post-operative thrombosis; and to promote patency of vascular grafts following surgery.

The active compounds are also useful as an addition to blood, blood products, blood substitutes, and other fluids which are used in artificial extra-corporeal circulation and perfusion of isolated body portions, e.g., limbs and organs, whether attached to the original body, detached and being preserved or prepared for transplant, or attached to a new body. It may also be used in laboratory animals, e.g. cats, dogs, rabbits, monkeys and rats, for these purposes in order to develop new methods and techniques for organ and limb transplants.

The active compounds also exhibit some vasodilatory action on blood vessels and therefore have a utility as anti-hypertensives for the treatment of high blood pressure in mammals, including man.

The amount of active compound required for therapeutic or prophylactic effect will vary with the route of administration, and the nature of the condition under treatment. In general a suitable dose for a mammal, including man, of active compound will lie in the range of 0.1 to 300 mg per kg body weight, particularly from 0.5 to 10 mg per kg body weight, for example 2 mg per kg. A suitable single oral dose for an adult human lies within the range of 50 to 600 mg, for example 150 mg given say three times a day.

While it is possible for the active compounds to be administered as the raw chemical it is preferable to present them as a pharmaceutical formulation. The formulations, both for veterinary and for human medical use, of the present invention comprise an active compound as above defined, together with one or more acceptable carriers therefor and optionally other therapeutic ingredients. The carrier(s) must be 'acceptable' in the sense of being compatible with the other ingredients of the formulation and not deleterious to the recipient thereof. Unit doses of a formulation may contain between 60 mg and 1.5 g of an active compound.

The formulations include those suitable for oral, rectal, vaginal or parenteral (including subcutaneous, intramuscular and intravenous) administration. Preferred formulations include tablets, capsules and injectable suspensions or solutions.

The formulations may conveniently be presented in unit dosage form and may be prepared by any of the methods well known in the art of pharmacy. All methods include the step of bringing into association the active compound (in the form of the base or a pharmaceutically acceptable acid addition salt) with the carrier which constitutes one or more accessory ingredients. In general the formulations are prepared by uniformly and intimately bringing into association the active compound with liquid carriers or finely divided solid carriers or both, and then, if necessary, shaping the product into the desired formulation.

It will be appreciated from the foregoing that the present invention provides the following features:

(a) Imidazole of formula (I) or a pharmaceutically acceptable acid addition salt thereof as an active agent for the treatment of a thromboembolic disorder in a mammal or mammalian tissue, including man or human tissue.

(b) Methods of preparing the imidazoles of formula (I) and acid addition salts thereof.

(c) Pharmaceutical formulations contain the imidazoles of formula (I) or as pharmaceutically acceptable acid addition salts thereof and a pharmaceutically acceptable carrier therefor.

(d) Method of preparing a pharmaceutical formulation according to (c).

(e) A method for the treatment or prophylaxis of a thrombo-embolic disorder in a mammal or mammalian tissue, including man or human tissue, comprising administering an active compound.

(f) Novel imidazoles of formula (I) in which n is 1 and A and R together form an alkenyl radical of from 5 to 9 carbon atoms.

(g) Novel imidazoles of formula (I) in which n is 0 (zero) and R is a cycloalkyl or cycloalkenyl group of from 5 to 9 carbon atoms, optionally substituted by one, two, three or more alkyl radicals each containing from 1 to 4 carbon atoms, preferably with the provisor that R is not unsubstituted cyclohexyl, or with the alternative proviso that R is not substituted or unsubstituted cyclohexyl.

The following Examples are provided by way of an illustration of the present invention and should in no way be construed as constituting a limitation thereof. All temperatures are given in degrees Celcius.

EXAMPLE 1

1-Cyclo-octylmethylimidazole

Cyclooctane methyl bromide (5.5 g, 0.027 mole) was added dropwise to a refluxing solution of imidazole (2.0 g, 0.03 mole) in a solution of sodium (0.7 g, 0.03 mole) in absolute ethanol (50 ml). After addition the mixture was refluxed for a further 15 hours.

The solid material was filtered off and the filtrate was concentrated under vacuum. Residue taken up in 2 N hydrochloric acid (100 ml) and washed with ether (25 ml). The aqueous layer was basified by the addition of 10 N aqueous sodium hydroxide solution and then extracted with chloroform (3×50 ml). Combined extracts dried over anhydrous magnesium sulphate and chloroform removed under vacuum. Residual oil purified on a silica gel column eluted with ethyl acetate/methanol (9:1). Product distilled under vacuum. B.p. 120°-122° C./0.2 mmHg.

EXAMPLE 2

Preparation of 1-(cyclopentylmethyl)imidazole

A solution of sodium ethoxide was made by dissolving sodium (2.3 g, 0.1 mole) in absolute ethanol (100 ml). Imidazole (6.8 g, 0.1 mole) was then added. The mixture was heated under reflux and cyclopentylmethylbromide (16.3 g, 0.1 mole) was added dropwise. The reaction mixture was allowed to reflux for a further 16 hours after addition. The mixture was then left to cool.

The solid material was then filtered off and the filtrate evaporated down under vacuum. The residue was taken up in 2 N HCl (150 ml) and washed with ether (50 ml). The solution was basified with excess 10 N NaOH and the product extracted with chloroform (3×50 ml). Combined extracts were dried over anhydrous $MgSO_4$ and chloroform removed under vacuum to give yellowish oil.

The crude product was purified on a silica gel column eluted with EtOAc/MeOH (9:1). The product fractions were combined and evaporated down under vacuum to leave 1.9 g of slightly yellowish oil. This was distilled under vacuum. B.pt. 68°-69° C./0.125 mmHg. Yield 0.95 g.

EXAMPLE 3

Preparation of 1-(3-cyclopentylpropyl)imidazole

A solution of sodium ethoxide was prepared by dissolving sodium (0.34 g, 0.0148 mole) in absolute ethanol (30 ml). Imidazole (1.0 g) was then added. The mixture was heated under reflux and 3-cyclopentylpropyl bromide (2.94 g, 0.0153 mole) was added dropwise. The reaction mixture was allowed to reflux for a further 20 hours after addition. The mixture was then allowed to cool.

The solid material was filtered off and the filtrate evaporated down under vacuum. Residue taken up in 2 N HCl (50 ml) and washed with ether (25 ml). The solution was basified with excess 10 N NaOH and the product extracted with chloroform (3×25 ml). Combined extracts were dried over anhydrous $MgSO_4$ and chloroform removed under vacuum to give 2.1 g golden-yellow oil.

The crude product was purified on a silica gel column eluted with EtOAc/MeOH (9:1). The product fractions were combined and evaporated down under vacuum to 1.25 g of slightly yellowish oil. This was distilled under vacuum. B.pt. 89°–90° C./0.1 mmHg. Yield 0.78 g.

EXAMPLE 4

Preparation of 1-(cycloheptylmethyl)imidazole

| Potassium t-butoxide | (3.1 g, 0.0277 mole) |
| Imidazole | (1.90 g, 0.0279 mole) |
| Cycloheptylmethyl bromide | (5.3 g, 0.02775 mole) |
| Dry N-butanol | (50 ml) |
| Dry nitrogen | |

Cycloheptylmethyl bromide (5.3 g, 0.02775 mole) was added dropwise to a mixture of potassium t-butoxide (3.1 g, 0.0277 mole) and imidazole (1.9 g, 0.0279 mole) in dry n-butanol, the temperature of the oil bath being 120° C. After the addition (about 20 minutes) the temperature of the reaction mixture was raised to boiling, and stirring, and heating under reflux was continued for 7 hours, when examination by t.l.c. showed that no further reaction had taken place.

The insoluble material was filtered off, and the butanol was removed under reduced pressure to afford a pale yellow oil.

The oil was dissolved in 2 N-HCl (100 ml) and the acid solution washed with ether (100 ml). The acid solution was then basified with 10 M NaOH, and the resulting oil extracted with chloroform (3×50 ml). The chloroform extracts were combined and dried.

Evaporation of the chloroform solution afforded 2.0 g pale yellow oil. T.l.c. shows imidazole still present. The oil was applied to a silica column and eluted with EtOAc/MeOH 9:1.

Evaporation of the fractions containing pure 1-(cycloheptylmethyl)imidazole afforded 1.3 g pale yellow oil. Distillation of the oil under reduced pressure afforded a colourless oil. B.p. 92°–94° C./0.1 mmHg. Yield 0.63 g.

EXAMPLE 5

(a) Preparation of 2-cyclooctenyl methanol (using the prins reaction NCHIDA Etal. Bull Chem. Soc. Jap. 46, 2512 (1973))

To a stirred suspension of paraformaldehyde (24 g; 0.64 mol) in 98% formic acid (100 cm$^3$) was added dropwise with stirring cyclooctene (69 g; 0.64 mol). After addition the mixture was stirred under reflux for 2 hours. After addition of water (100 cm$^3$) and ether (50 cm$^3$) the mixture was separated. The ether layer was washed with saturated NaHCO$_3$ solution (5×50 cm$^3$), water (2×50 ml) and dried over anhydrous MgSO$_4$. The ether was removed under vacuum and the residue distilled. Six fractions and residue were obtained.

| Fraction 1-Bp. <80°/24 mmHg | Combined via TLC |
| Fraction 2-Bp. 80°–110°/24 mmHg | Yield 21.5 g |
| Fraction 3-Bp. 110°–130°/0.5 mmHg | |
| Fraction 4-Bp. 110°–116°/0.3 mmHg | Combined via TLC |
| Fraction 5-Bp. 116°–130°/0.3 mmHg | Yield 45.3 g |
| Fraction 6-Bp. 130°–170°/0.3 mmHg | |

Fractions 1 and 2 were combined and 10 g were treated with Claisen alkalia (KOH {10 g} MeOH {31.2 cm$^3$} water {8 cm$^3$}). The mixtures refluxed for 2 hours when TLC showed no further change. The mixture was cooled, poured onto ice water (50 cm$^3$) and extracted with ether (3×50 cm$^3$). The combined extracts were dried over anhydrous MgSO$_4$ and the ether removed under vacuum to leave a colourless oil, yield 8.1 g, which was distilled under vacuum to give

| Fraction 8-Bp. <128°/23 mmHg | Combined |
| Fraction 9-Bp. 128–130°/23 mmHg | via TLC |
| Fraction 10-Bp. 130–132°/23 mmHg | Yield 6.7 g |

NMR on fraction 9 showed it to be slightly impure: possibly a trace of cyclooctane methanol or hexamethylene dioxane was present.

(b) Preparation of 2-cyclooctenyl methyl bromide

A solution of phosphorus tribromide (1.02 cm$^3$; 0.0105 m) in 40 to 60 petroleum ether (5 cm$^3$) was added dropwise to a solution of 2-cyclooctenylcarbinol (2.8 g; 0.02 m) (fraction 9 above) and AR. Pyridine (0.104 g; 0.0013 m) in petroleum ether (15 cm$^3$) stirred and cooled to $-10°$ C. After addition the mixture was allowed to warm to room temperature and stood for 2 days. The reaction mixture was treated with water (50 cm$^3$) and the organic layer separated. The aqueous layer was extracted with 40 to 60 petroleum ether (3×25 cm$^3$) and the combined organic layer and petrol extracts washed with 2 N-NaOH (25 cm$^3$) and water (25 cm$^3$). The petrol extracts were combined and dried over anhydrous MgSO$_4$ and the solvent removed under vacuum to leave a crude product 2.3 g. The crude product was distilled to give 0.7 g of pure product b.p. 48°–50°/0.25 mmHg.

(c) Preparation of 1-(2-cyclooctenylmethyl)imidazole

2-Cyclooctenylmethyl bromide (0.7 g; 0.0035 mole) as just made was added dropwise to a refluxing solution of imidazole (0.24 g; 0.0025 mole) and potassium tertiary butoxide (0.39 g; 0.0035 mole) in dry butanol under nitrogen. After addition the mixture was stirred under reflux for 1 hour. Pure product was obtained as described in Example 4, b.p. 108°–110°/0.02 mmHg.

EXAMPLE 6

Preparation of 1-(4-methylcyclohexylmethyl)imidazole

4-Methylcyclohexylmethyl bromide (3.1 g; 0.0164 M) was added dropwise to a refluxing solution of imidazole (1.12 g; 0.0165 M) in a solution of potassium tertiary butoxide (1.85 g; 0.0165 M) in n-butanol (50 cm$^3$). The reaction mixture was kept under dry nitrogen. After addition the mixture was heated under reflux for a further 2 hours and stood overnight at room temperature. TLC showed reaction half complete. The mixture was refluxed for a further 8 hours and stood over weekend at room temperature. TLC showed no further reaction was occurring. Insoluble material was filtered off, and solvent removed under vacuum. Residue taken up in 2 N-HCl (100 cm$^3$) and washed with ether (50 ml). Aqueous layer basified with excess 10 N NaOH and extracted with chloroform (3×50 cm$^3$). Combined extracts were dried over anhydrous MgSO$_4$ and solvent removed under vacuum. Oily residue was run on a silica gel column and eluted with EtOAc/MeOH 9:1. 0.8 g of column product obtained and was distilled to give 0.28 g of pure product having b.p. 80° C. at 0.125 mmHg.

EXAMPLE 7

Biological Results

Horse platelets were prepared from whole horse blood by differential centrifugation. Approximately $10^6$ platelets were homogenised in 1 ml 100 mM Tris buffer pH 7.4. Various concentrations of active compound were added and the reaction sets incubated for 5 minutes at ambient temperature. To each acid tube was added 20 nM of arachidonic acid containing $10^6$ DPM of labelled arachidonic acid and the tubes incubated for 3 minutes at 37° C. in a shaking water bath. After incubation the radioactive products were extracted from the acidified aqueous phase with ethyl acetate and after concentration resolved by thin layer chromotography on silica gel with chloroform/methanol/acetic acid/water (90:8:1:0.8) as a developing solvent. The amount of thromboxane produced was measured by scraping the radioactive zone corresponding to thromboxane $B_2$ and estimating the radioactivity in a liquid scintillation counter.

The concentration of active compound to reduce the enzyme activity by 50% ($ED_{50}$) was established. The results are shown in Table A.

The selectivity of the active compounds was measured in a similar manner to that described above and the amount of PGE, PGF and PGD produced was determined. The greater the selectivity, the more of the prostaglandins are produced indicating lower inhibition of cyclo-oxygenase.

The $ED_{50}$ and Selectivity results are shown in Table A in which O indicates no selectivity; + low selectivity; + + medium selectivity; and + + + high selectivity.

TABLE A

| Compound (Reference Compound) | $ED_{50}$ µg/ml | Selectivity |
|---|---|---|
| (Imidazole) | ≧500 | 0 to + |
| (1-Methylimidazole) | ≧200 | + + |
| 1-Cycloheptylimidazole | ~6 | + + |
| 1-Cyclopentylmethylimidazole | ~5 | + + + |
| 1-Cyclohexylethylimidazole | 4 | + + + |
| 1-Cyclooctylmethylimidazole | 4 | + + + |
| 1-Cyclohex-3-enylmethylimidazole | ~5 | + + + |
| 1-Cyclobutylmethylimidazole | 50 | + + + |
| 1-Cyclopentylimidazole | 125 | + + + |

EXAMPLE 8

Table formulation

| 1-Cyclooctylmethylimidazole (as a salt) | 150 mg |
|---|---|
| Starch | 25 mg |
| Polyvinylpyrrolidone | 2 mg |
| Magnesium stearate | 3 mg |

The imidazole salt is ground to a fine powder, blended with the starch and then the mixture granulated with an aqueous solution of the polyvinylpyrrolidone. The granules are sieved 1000µ, dried, sieved again and the magnesium stearate added. The mixture is then compressed into tablets.

In the same manner, tablets of 1-cyclohex-3-enylmethylimidazole and 1-cyclohexylethylimidazole are prepared.

EXAMPLE 9

Tablet formulation

Tablets (150 mg) of the imidazoles described in the preceding example are prepared as in the same manner from the following ingredients:

| The Imidazole Compound (as a salt) | 150 mg |
|---|---|
| Lactose | 100 mg |
| Starch | 30 mg |
| Polyvinylpyrrolidone | 2 mg |
| Magnesium stearate | 3 mg |

In the preparation, the lactose is blended with the starch.

EXAMPLE 10

Tablet formulation

Tablets (100 mg) of the imidazoles of Example 8 are prepared in the same manner from the following ingredients:

| The Imidazole Compound (as a salt) | 100 mg |
|---|---|
| Sodium starch glycolate | 10 mg |
| Polyvinylpyrrolidone | 2 mg |
| Magnesium stearate | 3 mg |

EXAMPLE 11

Tablet formulation

Tablets (150 mg) of the imidazoles of Example 8 are prepared in the same manner from the following ingredients, except that the starch, pregelled starch and imidazole compound are all blended together prior to granulation:

| The Imidazole Compound (as a salt) | 150 mg |
|---|---|
| Starch | 25 mg |
| Pregelled starch | 5 mg |
| Magnesium stearate | 3 mg |

EXAMPLE 12

Injectable formulation

| Imidazole compound of formula (I) | 15.0 g |
|---|---|
| Lactic Acid B.P. | q.s. to pH 3.0 |
| Water for Injections for B.P. | to 100.0 ml |

Suspend the compound in ¾ of the available quantity of water. Add sufficient Lactic Acid to dissolve the compound and to reduce the pH to 3.0. Dilute to volume with Water for Injections.

Sterilise the solution by passage through a membrane filter, pore size 0.22 µm.

Distribute the solution using aseptic precautions into sterilised ampoules, 1 ml per ampoule. Seale by fusion of the glass.

Each 1 ml ampoule supplies 150 mg of the imidazole compound: 1-cyclooctylmethylimidazole fumarate.

EXAMPLE 13

Injectable formulation

| Imidazole compound of formula (I) | 15.0 g |
|---|---|
| Citric Acid B.P. | q.s. to pH 3.0 |
| Chlorocresol | 0.1 g |
| Water for Injections to | 100.0 ml |

Suspend the compound in ½ the final volume of Water for Injections. Add sufficient Citric Acid as a 10% solution in Water for Injections to dissolve the compound andreduce the pH to 3.0. Dilute to volume with Water for Injections.

Sterilise the solution by passage through a membrane filter, pore size 0.22 μm.

Distribute the solution with aseptic precautions into sterilised vials, 25 ml per vial. Stopper with sterile rubber closures and seal with an aluminium cap.

Each 1 ml of solution provides 150 mg of the compound: 1-cyclooctylmethylimidazole fumarate

EXAMPLE 14

Injectable formulation

In the manner described in the preceding two Examples, injectable formulations of 1-cyclohexylethylimidazole and 1-cyclohex-3-enylmethylimidazole salts were prepared.

EXAMPLE 15

(a) 1-n-Butylimidazole

Bromobutane (27.4 ml; 0.255 mole) was added dropwise to a stirred solution of imidazole (13.6 g; 0.2 mole) in a mixture of methanol (30 ml) and sodium hydroxide solution (30 ml; 10M) maintained at 30° to 40° C. When the addition was complete the reaction mixture was stirred and refluxed for 12 hours. The solvent was evaporated, the residue extracted with chloroform (2×50 ml) and the extracts dried over magnesium sulphate and concentrated under reduced pressure. The resulting yellow oil was purified to give 1-n-butylimidazole as a colourless oil, b.p. 122°-123° C./20 mmHg.

(b) 1-n-Butylimidazole oxalate

To 1-n-butylimidazole (0.31 g; 0.0025 mole) in methanol (5 ml) was added oxalic acid (0.225 g; 0.0025 mole) in methanol (5 ml). After heating under reflux for 5 minutes the mixture was evaporated under reduced pressure to afford a white solid. Recrystallisation of the solid from ethanol/ether (1:4) afforded 1-n-butylimidazole oxalate as colourless needles, m.p. 82° to 83° C. (Found: C,50.2; H,6.5; N,13.05. Calc. for $C_9H_{14}N_2O_4$:C,50.45; H,6.55; N,13.1%).

(c) 1-n-Butylimidazole perchlorate

To 1-n-butylimidazole (0.31 g; 0.0025 mole) in methanol (5 ml) was added perchloric acid (0.33 g, 70%) in methanol (3 ml). After boiling for 5 minutes, the mixture was evaporated under reduced pressure to afford a white solid. Recrystallisation of the solid from ethyl acetate/ether (1:4) afforded 1-n-butylimidazole perchlorate as a white solid, m.p. 54° to 55° C. (Found: C,37.25; H,5.95; N,12.55. Calc. for $C_7H_{13}ClN_2O_4$: C,37.4; H,5.8; N,12.45).

EXAMPLE 16

By the method described in Example 15 above the following compound was prepared:

1-(3-Methylbutyl)imidazole, b.p. 62°-64° C./0.2 mmHg. In place of sodium hydroxide, sodium bicarbonate was used.

EXAMPLE 17

1-Crotylimidazole

Crotyl chloride (3.2 g; 35 m mole) in methanol (35 ml) was added dropwise with stirring during 3.5 hours to a refluxing mixture of imidazole (11.9 g; 175 m mole) and sodium bicarbonate (2.95 g; 35 m mole) in methanol (35 ml). When the addition was complete the reaction mixture was refluxed for 24 hours, the solvent evaporated and the residue dissolved in water (60 ml) and extracted with chloroform (3×20 ml). The combined extracts were washed with saturated aqueous sodium chloride solution (25 ml), dried over magnesium sulphate and concentrated under reduced pressure. The residue was fractionally distilled to yield 1-crotylimidazole as a colourless oil, b.p. 123°-124° C./18 mmHg.

EXAMPLE 18

(a) 1-n-Pentylimidazole (1-n-Amylimidazole)

n-Pentylbromide (30 ml; 0.24 mole) was added dropwise to a stirred solution of imidazole (13.6 g; 0.2 mole) in a mixture of methanol (30 ml) and sodium hydroxide solution (30 ml, 10M) maintained at 20° C. When the addition was complete the reaction mixture was stirred and refluxed for 24 hours. The solvent was evaporated, the residue extracted with chloroform (2×50 ml) and the solid remaining removed by filtration. The chloroform solution (filtrate) was dried over magnesium sulphate and concentrated to give a yellow oil which on purification gave 1-n-pentylimidazole as a colourless oil, b.p. 66°-68° C./0.15 mmHg.

(b) By the method described in (a) above the following compound was prepared:

1-n-Hexylimidazole, b.p. 78°-80° C./0.2 mmHg.

EXAMPLE 19

1-Cyclohexylmethylimidazole

Bromomethylcyclohexane (39.8 g; 0.225 mole) was added dropwise to a refluxing solution of imidazole (13.6 g; 0.2 mole) and sodium (4.6 g; 0.2 mole) in absolute ethanol (100 ml). After addition the reaction mixture was heated under reflux for a further 5 hours. After this period the mixture was cooled and the solvent evaporated under reduced pressure. The residue was taken up in water (150 ml), washed with ether (50 ml) and extracted with chloroform (3×50 ml). The combined chloroform extracts were dried over anhydrous magnesium sulphate and evaporated under reduced pressure to leave a residual yellow oil as crude product which was purified to give the product as a colourless oil b.p. 86°-90° C./0.2 mmHg. The product solidified on cooling, m.p. 25° to 30° C.

EXAMPLE 20

1-Cycloheptylimidazole

Cycloheptyl bromide (10.0 g, 0.0565 mole) was added dropwise to a refluxing mixture of imidazole (385 g, 0.0565 mole) and sodium bicarbonate (4.75 g, 0.0565 mole) im methanol (100 ml). After addition was complete the mixture was heated under reflux for a further 24 hours.

The mixture was then cooled and the solvent removed under vacuum. The residue was taken up in 2 N hydrochloric acid (150 ml) and washed with ether (50 ml). The aqueous layer was basified by the addition of aqueous 10 N sodium hydroxide solution and then extracted with chloroform (3×50 ml). The combined extracts were dried over anhydrous magnesium sulphate and the chloroform was then removed under vacuum. Residual oil purified on a silica gel column eluted with ethyl acetate/methanol (9:1). The product was collected and distilled under vacuum. B.p. 102°-104° C./0.15 mmHg. Solidified on cooling to white solid. M.p. 31° to 35° C.

EXAMPLE 21

Preparation of 1-(cyclopentyl)imidazole

Imidazole (6.8 g, 0.1 mole) was dissolved in 100 ml of dry dimethylformamide (DMF). Sodium hydride, 50% dispersion in oil, (4.8 g, 0.1 mole) was added in small portions and the mixture was allowed to stir for 15 minutes. Cyclopentyl bromide (14.9 g, 0.1 mole) dissolved in 100 ml dry DMF was then added dropwise to the mixture which was kept under nitrogen and at about room temperature. Allowed to stir for a further 1 hour. When t.l.c. showed no further reaction, the mixture was poured onto approximately equal volume of water and shaken well. The product was then extracted with chloroform (3×200 ml) and dried over anhydrou $MgSO_4$. The dry extract was evaporated down under vacuum. The DMF was then distilled off at 15 mmHg pressure to leave a yellowish oil. T.l.c. showed that the mixture was mainly product and an imidazole impurity, about 10 g nn on silica gel column with MeOH/EtOAC 1:9. Product fractions were combined and evaporated. Residual oil obtained was distilled under vacuum. B.pt. 67°-68° C./0.2 mm. Yield 2.0 g.

EXAMPLE 22

Preparation of 1-(pent-2-enyl)imidazole

Pent-2-enyl bromide (18.5 g) was added dropwise to a stirred refluxing mixture of imidazole (10 g) and sodium bicarbonate (12.4 g) in methanol (50 ml). After addition was complete, the mixture was stirred under reflux for a further 24 hours. The mixture was filtered to remove unsoluble material and the filtrate evaporated to remove solvent. Residue taken in 2N-HCl (150 ml) and washed with ether (50 ml). The aqueous layer was basified with 10N NaOH and extracted with chloroform (3×50 ml). Combined extracts dried over anhydrous $MgSO_4$ and chloroform removed under vacuum to leave crude product which was purified on silica gel column (EtOAc/MeOH 9:1 was used as eluent). Product fractions were collected; total weight 4.9 g. 1.0 g was distilled under vacuum; yield 1.08 g. B.p. 134° C./15 mmHg. Micro analysis: $C_8H_{12}N_2$ requires C,70.59; H,8.82; N,20.59. Found: C,69.72, H,8.88; N,20.43.

EXAMPLE 23

Preparation of 1-(pent-4-enyl)imidazole

Pent-4-enyl bromide (10 g, 0.067 mole) was added dropwise to a stirred refluxing mixture of imidazole (9 g; 0.132 mole) and sodium bicarbonate (11 g; 0.13 mole) in methanol (50 ml). After addition the mixture was stirred for a further 50 hours under reflux. The reaction mixture was filtered to remove the insoluble matter and the filtrate evaporated to a yellow oil. This oil was taken up in 2M HCl (150 ml) and washed with ether (50 ml). The acid solution was then basified with 10M NaOH (about 30 ml) and extracted with chloroform (3×50 ml). The combined extracts were dried over anhydrous $MgSO_4$ and the solvent removed under vacuum to leave a yellow oil as crude product, which was purified on silica gel column using 10% MeOH/EtOAc as eluent. 1.0 g distilled in vacuo b.p. 132°/12 mm, yield 0.9 g. Micro analysis: $C_8H_{12}N_2$ requires C,70.59, H,8.82, N,20.59. Found: C,69.24, H,8.56, N,20.11.

EXAMPLE 24

Further Biological Results

By the method described in the Biological Results in Example 7 above, the $ED_{50}$ values were obtained for the compounds set out in Table I.

TABLE I

| Active compound (Reference compound) | $ED_{50}$ μg/ml |
| --- | --- |
| (Imidazole) | ≧500 |
| (1-methylimidazole) | ≧200 |
| 1-n-Butylimidazole | 10 |
| 1-n-Pentylimidazole | 7 |
| 1-n-Hexylimidazole | 10 |
| 1-Pent-2-enylimidazole | 10 |
| 1-Pent-4-enylimidazole | 23 |
| 1-(3-Methylbutyl)imidazole | 20 |
| 1-Cyclohexylmethylimidazole | 2.5 |

EXAMPLE 25

Tablet formulations

By the methods described in the Tablet formulation Examples described above, tablets were prepared of:
1-m-butylimidazole
1-(3-methylbutyl)imidazole
1-crotylimidazole
1-n-pentylimidazole
1-cyclohexylmethylimidazole
1-cyclopentylimidazole
1-cycloheptylimidazole
1-(pent-2-enyl)imidazole
1-(pent-4-enyl)imidazole.

In each case the imidazole was present as a salt, e.g. the fumarate or perchlorate.

EXAMPLE 26

Injectable formulations

Injectable formulations were prepared by the method of the Injectable formulation in Example 12 above using the imidazoles mentioned in the immediately preceding Example.

What we claim is:

1. A method for the treatment or prophylaxis of a thrombo-embolic disorder of a mammal or a mammalian tissue comprising the administration to the mammal or mammalian tissue of a non-toxic, anti-thrombo-embolic amount of an imidazole of the formula

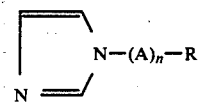

in which A is a straight or branched, saturated or unsaturated acyclic hydrocarbon radical of from 1 to 3 carbon atoms, n is 0 or 1, and R is a cycloalkyl or cycloalkenyl radical of from 4 to 9 carbon atoms and optionally substituted by one two, three or more alkyl radicals each containing from 1 to 4 carbon atoms, or, when n is 1, A and R together form an alkyl radical of from 4 to 7 carbon atoms or an alkenyl or alkynyl radical of from 4 to 9 carbon atoms, the imidazole being the free base or a pharmaceutically acceptable salt thereof.

2. A method as claimed in claim 1 wherein n is 1, A is a straight or branched, saturated or unsaturated acyclic hydrocarbon radical of from 1 to 3 carbon atoms and R is a cycloalkyl or cycloalkenyl radical of from 4 to 9 carbon atoms optionally substituted by one, two, three or more alkyl radicals each containing from 1 to 4 carbon atoms, the imidazole being the free base or a pharmaceutically acceptable salt thereof.

3. A method as claimed in claim 1 wherein n is 1, A is selected from —CH$_2$— and —(CH$_2$)$_2$— and R is selected from a cycloalkyl or cycloalkenyl radical containing from 6 to 8 carbon atoms.

4. A method as claimed in claim 1 wherein the imidazole is selected from 1-cyclooctylmethylimidazole, 1-cyclohexylethylimidazole and 1-cyclohex-3-enylmethylimidazole, 1-cycloheptylmethylimidazole, and pharmaceutically acceptable acid addition salts thereof.

5. A method as claimed in claim 1 wherein the imidazole or a pharmaceutically acceptable salt thereof is administered orally to a mammal.

6. A method as claimed in claim 1 wherein the imidazole or a pharmaceutically acceptable salt thereof is administered parenterally to a mammal.

7. A method as claimed in claim 1 wherein the mammal or mammalian tissue is man or human tissue respectively.

8. A method as claimed in claim 1 wherein the imidazole or a pharmaceutically acceptable salt thereof is administered to a mammal in an amount of from 0.1 to 300 mg per kg body weight of mammal, said amount of dose being the amount of imidazle base.

9. A method as claimed in claim 8 wherein the amount is from 0.5 to 10.0 mg per kg body weight of mammal, said dose calculated as base.

10. A method as claimed in claim 1 comprising the treatment or prophylaxis of thrombosis.

11. A method as claimed in claim 1 comprising the treatment or prophylaxis of cerebro-vascular thrombosis.

12. A method as claimed in claim 1 comprising the treatment or prophylaxis of myocardial infarction.

13. A method as claimed in claim 1 comprising the treatment or prophylaxis of peripheral vascular disease.

14. A method for the treatment or prophylaxis of a thrombo-embolic disorder of a mammal including man comprising the administration to the mammal of a non-toxic, anti-thrombo-embolic amount of 1-cyclooctylmethylimidazole or a pharmaceutically acceptable acid addition salt thereof.

15. A method as claimed in claim 14 wherein the thrombo-embolic disorder is myocardial infarction.

16. A method as claimed in claim 14 wherein the thrombo-embolic disorder is cerebro-vascular thrombosis.

17. A method as claimed in claim 14 wherein the thrombo-embolic disorder is ischaemic peripheral vascular disease.

18. A pharmaceutical formulation, for the treatment or prophylaxis of a thrombo-embolic disorder in a mammal comprising a non-toxic, anti-thrombo-embolic amount of an imidazole of the formula

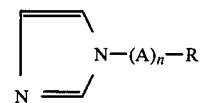

in which A is a straight or branched, saturated or unsaturated acyclic hydrocarbon radical of from 1 to 3 carbon atoms, n is 0 or 1, and R is a cycloalkyl or cycloalkenyl radical of from 4 to 9 carbon atoms and optionally substituted by one, two, three or more alkyl radicals and containing from 1 to 4 carbon atoms, or, when n is 1, A and R together form n alkyl radical of from 4 to 7 carbon atoms or an alkenyl or alkynyl radical from 4 to 9 carbon atoms, the imidazole being the free base or a pharmaceutically acceptable salt thereof, together with a pharmaceutically acceptable carrier therefor.

19. A pharmaceutical formulation as claimed in claim 18 wherein n is 1, A is a straight or branched saturated or unsaturated acyclic hydrocarbon radical of from 1 to 3 carbon atoms and R is a cycloalkyl or cycloalkenyl radical of from 4 to 9 carbon atoms optionally substituted by one, two, three or more alkyl radicals each containing from 1 to 4 carbon atoms, the imidazole being the free base or a pharmaceutically acceptable salt thereof, together with a pharmaceutically acceptable carrier therefor.

20. A pharmaceutical formulation as claimed in claim 18 wherein n is 1, R is selected from a cycloalkyl and a cycloalkenyl radical of from 6 to 8 carbon atoms, and A is —CH$_2$— or —(CH$_2$)$_2$—.

21. A pharmaceutical formulation as claimed in claim 18 wherein the imidazole is selected from 1-cyclooctylmethylimidazole, 1-cyclohexylethylimidazole, 1-cycloheptylmethylimidazole and 1-cyclohex-3-enylmethylimidazole and pharmaceutically acceptable and acid addition salts thereof.

22. A pharmaceutical formulation as claimed in any of claims 18 to 21 in the form of a tablet.

23. A pharmaceutical formulation as claimed in any of claims 18 to 21 in the form of a parenterally acceptable injectable solution or suspension.

24. A pharmaceutical formulation as claimed in any of claims 18 to 21 in the form of a capsule.

25. A pharmaceutical formulation for the treatment or prophylaxis of a thrombo-embolic disorder in a mammal comprising a non-toxic, anti-thrombo-embolic amount of 1-cyclooctylmethylimidazole or a pharmaceutically acceptable acid addition salt thereof, in association with a pharmaceutically acceptable carrier therefor.

26. A tablet for the treatment or prophylaxis of a thrombo-embolic disorder in a mammal having a non-toxic, anti-thrombo-embolic amount of 1-cyclooctylmethylimidazole or a pharmaceutically acceptable salt thereof.

27. A tablet as claimed in claim 26 containing from 50 to 600 mg of the imidazole or a pharmaceutically acceptable salt thereof, said amount being calculated as the free base.

28. A tablet as claimed in claim 27 wherein the amount is 150 mg.

29. The pharmaceutical formulation of claim 18 wherein said imidazole is 1-Cyclohexylethylimidazole or a pharmaceutically acceptable salt thereof.

30. The pharmaceutical formulation of claim 18 wherein said imidazole is 1-Cyclopentylmethylimidazole or a pharmaceutically acceptable salt thereof.

31. A pharmaceutical formulation for the treatment or prophylaxis of a thromo-embolic disorder in a mammal comprising a non-toxic, anti-thrombo-embolic amount 1-Cyclooctylvinylimidazole or a pharmaceutically acceptable salt thereof in association with a pharmaceutically acceptable carrier therefor.

32. A pharmaceutical formulation for the treatment or prophylaxis of a thromo-embolic disorder in a mammal comprising a non-toxic, anti-thromo-embolic amount 1-Cyclooctylethyl) or a pharmaceutically acceptable salt thereof in association with a pharmaceutically acceptable carrier therefor.

33. A pharmaceutical formulation for the treatment or prophylaxis of a thromo-embolic disorder in a mammal comprising a non-toxic, anti-thromo-embolic amount 1-(2-Cycoolctylethyl) imidazole or a pharmaceutically acceptable salt thereof in association with a pharmaceutically acceptable carrier therefor.

34. A pharmaceutical formulation for the treatment or prophylaxis of a thromo-embolic disorder in a mammal comprising a non-toxic, anti-thromo-embolic amount 1-(3-Cyclooctylpropyl) imidazole or a pharmaceutically acceptable salt thereof in association with a pharmaceutically acceptable carrier therefor.

35. The pharmaceutical formulation of claim 18 wherein said imidazole is 1-(Cycloheptylmethyl)imidazole or a pharmaceutically acceptable salt thereof.

36. A pharmaceutical formulation for the treatment or prophylaxis of a thromo-embolic disorder in a mammal comprising a non-toxic, anti-thromo-embolic amount 1-Cyclononylmethylimidazole or a pharmaceutically acceptable salt thereof in association with a pharmaceutically acceptable carrier therefor.

37. The pharmaceutical formulation of claim 18 wherein said imidazole is 1-(4-Methylcyclohexylmethyl)imidazole or a pharmaceutically acceptable salt thereof.

38. A pharmaceutical formulation for the treatment or prophylaxis of a thromo-embolic disorder in a mammal comprising a non-toxic, anti-thromo-embolic amount 1-(Cyclobutylmethyl) imidazole or a pharmaceutically acceptable salt thereof in association with a pharmaceutically acceptable carrier therefor.

39. The pharmaceutical formulation of claim 18 wherein said imidazole is 1-Cyclohexylmethylimidazole or a pharmaceutically acceptable salt thereof.

40. The pharmaceutical formulation of claim 18 wherein said imidazole is 1-n-Butylimidazole or a pharmaceutically acceptable salt thereof.

41. The pharmaceutical formulation of claim 18 wherein said imidazole is 1-n-Pentylimidazole or a pharmaceutically acceptable salt thereof.

42. The pharmaceutical formulation of claim 18 wherein said imidazole is 1-n-Hexylimidazole or a pharmaceutically acceptable salt thereof.

43. The pharmaceutical formulation of claim 18 wherein said imidazole is 1-(3-Methylbutyl)imidazole or a pharmaceutically acceptable salt thereof.

44. The pharmaceutical formulation of claim 18 wherein said imidazole is 1-Cyclohex-3-enylmethylimidazole or a pharmaceutically acceptable salt thereof.

45. The pharmaceutical formulation of claim 18 wherein said imidazole is 1-(Cyclohept-2-enylmethyl)imidazole or a pharmaceutically acceptable salt thereof.

46. A pharmaceutical preparation in dosage unit form adapted for administration to obtain an anti-thrombo-embolic effect, comprising, per dosage unit, an anti-thrombo-embolic-effective non-toxic amount of a compound selected from the group consisting of
1-Cyclooctylmethylimidazole
1-Cyclohex-3-enylmethylimidazole
1-Cyclohexylethylimidazole
1-Cyclopentylmethylimidazole
1-Cyclooctylvinylimidazole
1-(1-Cyclooctylethyl)imidazole
1-(2-Cyclooctylethyl)imidazole
1-(3-Cyclooctylpropyl)imidazole
1-(Cycloheptylmethyl)imidazole
1(Cyclohept-2-enylmethyl)imidazole
1-Cyclonoylmethylimidazole
1-(4-Methylcyclohexylmethyl)imidazole
1-(Cyclobutylmethyl)Imidazole
1-Cycloheptylimidazole
1-Cyclopentylimidazole
1-Cyclohexylmethylimidazole
1-n-Butylimidazole
1-n-Pentylimidazole
1-n-Hexylimidazole
1-Pent-2-enylimidazole
1-Pent-4-enylimidazole
1-(3-Methylbutyl)imiazole
and pharmaceutically acceptable salts thereof and a pharmaceutically acceptable carrier.

47. A pharmaceutical preparation as recited in claim 46 wherein the amount of said compound is within the range from about 50 to about 600 milligrams, said amount calculated as base.

48. A pharmaceutical preparation in dosage unit form adapted for administration to obtain an anti-thrombo-embolic effec, comprising, per dosage unit, an anti-thrombo-embolic-effective non-toxic amount of an compound selected from the group consisting of an imidazole of the formula $$\begin{array}{c} \diagup \diagdown \\ \mid \quad \quad N-(A)_n-R \\ N \diagup\!\!\!= \end{array}$$

in which A is a straight or branched, saturated or unsaturated acyclic hydrocarbon radical of form 1 to 3 carbon atoms, n is 0 or 1, and R is a cycloalkyl or cycloalkenyl radical of from 4 to 9 carbon atoms and optionally substituted by one, two, three or more alkyl radicals each containing from 1 to 4 carbon atoms, or, when n is 1, A and R together form an alkyl radical of from 4 to 7 carbon atoms or an alkenyl or alkynyl radical of from 4 to 9 carbon atoms, the imidazole being the free base and pharmaceutically acceptable salts thereof and a pharmaceutically acceptable carrier.

49. A pharmaceutical preparation as recited in claim 48, wherein the amount of said compound is within the range from about 50 to about 600 milligrams, said amount calculated as base.

50. A pharmaceutical formulation for the treatment or prophylaxis of a thromo-embolic disorder in a mammal comprising a non-toxic, anti thromo embolic amount 1-Cyclohex-e-enylmethylimidazole or a pharmaceutically acceptable salt thereof in association with a pharmaceutically acceptable carrier therefor.

51. A pharmaceutical formulation for the treatment or prophylaxis of a thromo-embolic disorder in a mammal comprising a non-toxic, anti-thromo-embolic amount 1-(Cyclohept-2-enylmethyl) imidazole or a pharmaceutically acceptable salt thereof in association with a pharmaceutically acceptable carrier therefor.

52. The pharmaceutical formulation of claim 18 wherein said imidazole is 1-Pent-2-enylimidazole or a pharmaceutically acceptable salt thereof.

53. The pharmaceutical formulation of claim 18 wherein said imidazole is 1-Pent-4-enylimidazole or a pharmaceutically acceptable salt thereof.

54. A pharmaceutical formulation for the treatment or prophylaxis of a thromo-embolic disorder in a mammal comprising a non-toxic, anti-thromo-embolic amount 1-cyclopentylimidazole or a pharmaceutically acceptable salt thereof in association with a pharmaceutically acceptable carrier therefor.

55. A pharmaceutical formulation for the treatment or prophylaxis of a thromo-embolic disorder in a mammal comprising a non-toxic, anti-thromo-embolic amount 1-cycloheptylimidazole or a pharmaceutically acceptable salt thereof in association with a pharmaceutically acceptable carrier therefor.

56. The method of claim 1, wherein the imidazole is 1-Cyclohex-3-enylmethylimidazole or a pharmaceutically acceptable salt thereof.

57. The method of claim 1, wherein the imidazole is 1-cyclohexylethylimidazole or a pharmaceutically acceptable salt thereof.

58. The method of claim 1, wherein the imidazole is 1-cyclopentylmethylimidazole or a pharmaceutically acceptable salt thereof.

59. The method of claim 1, wherein the imidazole is 1-cyclooctylvinylimidazole or a pharmaceutically acceptable salt thereof.

60. The method of claim 1, wherein the imidazole is 1-(1-Cyclooctylethyl)imidazole or a pharmaceutically acceptable salt thereof.

61. The method of claim 1, wherein the imidazole is 1-(2-Cyclooctylethyl)imidazole or a pharmaceutically acceptable salt thereof.

62. The method of claim 1, wherein the imidazole is 1-(3-Cyclooctylpropyl)imidazole or a pharmaceutically acceptable salt thereof.

63. The method of claim 1, wherein the imidazole is 1-(Cycloheptylmethyl)imidazole or a pharmaceutically acceptable salt thereof.

64. The method of claim 1, wherein the imidazole is 1-(Cyclohept-2-enylmethyl)imidazole or a pharmaceutically acceptable salt thereof.

65. The method of claim 1, wherein the imidazole is 1-Cyclononylmethylimidazole or a pharmaceutically acceptable salt thereof.

66. The method of claim 1, wherein the imidazole is 1-(4-Methylcyclohexylmethyl)imidazole or a pharmaceutically acceptable salt thereof.

67. The method of claim 1, wherein the imidazole is 1-(Cyclobutylmethyl)imidazole or a pharmaceutically acceptable salt thereof.

68. The method of claim 1, wherein the imidazole is 1-Cycloheptylimidazole or a pharmaceutically acceptable salt thereof.

69. The method of claim 1, wherein the imidazole is 1-Cyclopentylimidazole or a pharmaceutically acceptable salt thereof.

70. The method of claim 1, wherein the imidazole is 1-Cyclohexylmethylimidazole or a pharmaceutically acceptable salt thereof.

71. The method of claim 1, wherein the imidazole is 1-n-Butylimidazole or a pharmaceutically acceptable salt thereof.

72. The method of claim 1, wherein the imidazole is 1-n-Pentylimidazole or a pharmaceutically acceptable salt thereof.

73. The method of claim 1, wherein the imidazole is 1-n-Hexylimidazole or a pharmaceutically acceptable salt thereof.

74. The method of claim 1, wherein the imidazole is 1-Pent-2-enylimidazole or a pharmaceutically acceptable salt thereof.

75. The method of claim 1, wherein the imidazole is 1-Pent-4-enylimidazole or a pharmaceutically acceptable salt thereof.

76. The method of claim 1, wherein the imidazole is 1-(3-Methylbutyl)imidazole or a pharmaceutically acceptable salt thereof.

* * * * *